United States Patent
Jorand-Lebrun et al.

(10) Patent No.: US 9,567,320 B2
(45) Date of Patent: Feb. 14, 2017

(54) PYRIDAZINONE-AMIDES DERIVATIVES

(71) Applicant: Merck Patent GmbH, Darmstadt (DE)

(72) Inventors: Catherine Jorand-Lebrun, Contamine-Sarzin (FR); Santosh Kulkarni, Bangalore (IN); Stefano Crosignani, Nivelles (BE)

(73) Assignee: MERCK PATENT GmbH, Darmstadt (DE)

( * ) Notice: Subject to any disclaimer, the term of this patent is extended or adjusted under 35 U.S.C. 154(b) by 0 days.

(21) Appl. No.: 14/766,671

(22) PCT Filed: Feb. 6, 2014

(86) PCT No.: PCT/EP2014/000316
§ 371 (c)(1),
(2) Date: Aug. 7, 2015

(87) PCT Pub. No.: WO2014/121931
PCT Pub. Date: Aug. 14, 2014

(65) Prior Publication Data
US 2015/0376167 A1    Dec. 31, 2015

(30) Foreign Application Priority Data
Feb. 7, 2013 (EP) .................................... 13154390

(51) Int. Cl.
| | |
|---|---|
| *A61K 31/501* | (2006.01) |
| *C07D 401/14* | (2006.01) |
| *C07D 403/14* | (2006.01) |
| *A61K 31/506* | (2006.01) |
| *A61K 45/06* | (2006.01) |

(52) U.S. Cl.
CPC ........... *C07D 403/14* (2013.01); *A61K 31/501* (2013.01); *A61K 31/506* (2013.01); *A61K 45/06* (2013.01); *C07D 401/14* (2013.01)

(58) Field of Classification Search
CPC ............................ C07D 401/14; C07D 403/14
See application file for complete search history.

(56) References Cited

U.S. PATENT DOCUMENTS

2006/0142292 A1    6/2006    Kyotani et al.

FOREIGN PATENT DOCUMENTS

| EP | 1 604 984 A1 | 12/2005 |
| WO | WO 2012/129258 A1 | 9/2012 |

OTHER PUBLICATIONS

U.S. Appl. No. 14/766,291, filed Aug. 6, 2015, Jorand-Lebrun, et al.
International Search Report issued Mar. 31, 2014, in PCT/EP2014/000316 filed Feb. 6, 2014.

*Primary Examiner* — Brian McDowell
(74) *Attorney, Agent, or Firm* — Oblon, McClelland, Maier & Neustadt, L.L.P.

(57) ABSTRACT

The present invention relates to compounds of formula (I) wherein R1, Ra, Rb and Z have the meaning given in claim 1, and their use in the prophylaxis and treatment of diseases.

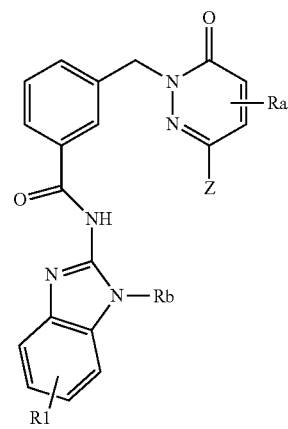

(I)

7 Claims, No Drawings

PYRIDAZINONE-AMIDES DERIVATIVES

The present invention provides Pyridazinone-amides derivatives of Formula (I) as IRAK inhibitors and their use in the treatment of cancer, and other diseases related to IRAK overexpression, like rheumatoid arthritis, systemic lupus erythematosus or lupus nephritis.

BACKGROUND

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAKI (Muzio et al., 1997. Science 278 (5343): 1612-5). IRAK3 (also called IRAKM) was identified using a murine EST sequence encoding a polypeptide with significant homology to IRAK1 to screen a human phytohemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that. IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

According to one aspect of the invention, are provided compounds of Formula (I).

According to another aspect of the invention, are provided compounds of Formula (I) which are suitable for the treatment and/or prevention of disorders related to IRAK.

According to another aspect of the invention, are provided compounds, which are able to modulate, especially inhibit the activity or function of IRAK in disease states in mammals, especially in humans.

According to another aspect of the invention, are provided methods for the treatment and/or prevention of disorders selected from auto-immune, inflammatory disorders, cardiovascular diseases, neurodegenerative disorders, bacterial and viral infections, allergy, asthma, pancreatitis, multiorgan failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I) which are selective of IRAK-4 and/or IRAK-1 over the other isoforms.

According to another aspect of the invention is provided a kit or a set comprising at least one compound of Formula (1), preferably in combination with immunomodulating agents. Preferably, the kit consists of separate packs of:

(a) an effective amount of a compound of the formula (I) and/or pharmaceutically usable derivatives, solvates, salts, hydrates and stereoisomers thereof, including mixtures thereof in all ratios, and (b) an effective amount of a further medicament active ingredient.

According to another aspect of the invention, is provided a process for the synthesis of compounds of Formulae (I) and related Formulae.

DETAILED DESCRIPTION OF THE INVENTION:

In one embodiment, the present invention provides a compound of Formula (I)

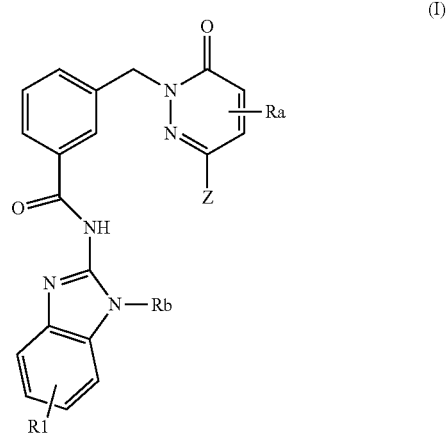

Wherein
Z denotes a group

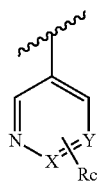

wherein
X is CH or N,
Y is CH or N,
Ra, Rc, R1 denote each independently H, Hal or Al,
Rb is H or alkyl
Al is branched or linear alkyl having 1 to 12 C-atoms, wherein one or more, such as 1 to 7, H atoms may be replaced by Hal, ORb, COORb, CN or N(Rb)$_2$ and wherein one or more, preferably 1 to 5 CH$_2$-groups may be replaced by O, CO, NRb or S, SO, SO$_2$, 1,2-, 1,3- or 1,4-phenylen, —CH═CH— or —C≡C—,
and
Hal denotes F, CI, Br, I
and pharmaceutically acceptable derivatives, solvates, tautomers, salts, hydrates and stereoisomers thereof, including mixtures thereof in all ratios.

The present invention includes in particular tautomeric form (I'):

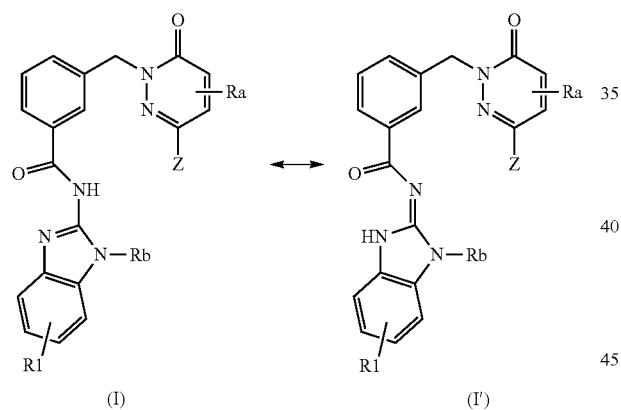

If not indicated otherwise, alkyl denotes a carbon chain having 1 to 12 carbon atoms, preferably 1 to 8 carbon atoms and most preferably 1 to 6 carbon atoms. Alkyl very preferably denotes methyl, furthermore ethyl, propyl, isopropyl, butyl, isobutyl, sec-butyl or tert-butyl, furthermore also pentyl, 1 , 2 or 3 methylbutyl, 1,1 , 1,2- or 2,2-dimethylpropyl, 1-ethylpropyl, hexyl, 1, 2, 3 or 4 methylpentyl, 1,1, 1,2, 1,3, 2,2, 2,3- or 3,3-dimethylbutyl, 1 or 2 ethylbutyl, 1 ethyl-1-methylpropyl, 1 ethyl-2-methylpropyl, 1,1,2- or 1,2,2-trimethylpropyl.

The group Oalkyl preferably denotes methoxy and ethoxy.

R is preferably methyl, ethyl, n-propyl or n-butyl.

Ra is preferably H, Hal ORd or alkyl, wherein Rd is H, alkyl or CORb.

R1 denotes preferably H, alkyl, Hal, Oalkyl, ORd, or (CH$_2$)$_n$CONHRb or (CH$_2$)$_n$COORb, wherein n is 0, 1, 2, 3, 4, 5, or 6 and Rb is as defined above and , wherein Rd is H, alkyl or CORb.

Rb is preferably H, methyl or ethyl.

Z preferably denotes pyridinyl or pyrimidinyl.

Above and below, all radicals and indices have the meaning indicated under the formula (I), unless expressly stated otherwise.

Generally, compounds of formula I are the more preferred, the more preferred substituents they carry.

Preferred compounds 1 to 17 of formula I are given below together with their activities (IC$_{50}$ values were obtained according to the IRAK 1 and IRAK 4 enzymatic assays described in Example 18):

| Example | Compound | IC$_{50}$ IRAK1 | IC$_{50}$ IRAK4 |
|---|---|---|---|
| 1 | | ** | *** |
| 2 | | *** | ** |
| 3 | | nd | * |

| Example | Compound | IC50 IRAK1 | IC50 IRAK4 |
|---|---|---|---|
| 4 | 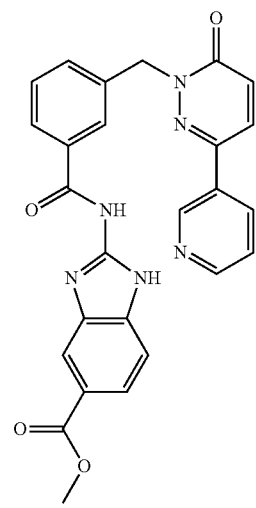 [SMILES: COC(=O)c1ccc2[nH]c(NC(=O)c3cccc(Cn4nc(-c5cccnc5)ccc4=O)c3)nc2c1] | nd | * |
| 5 | 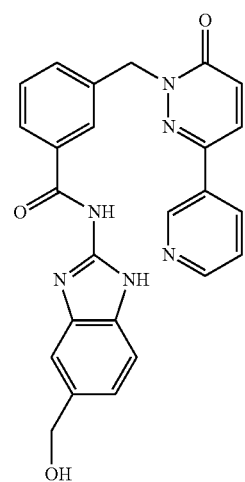 [SMILES: O=C(Nc1nc2cc(CO)ccc2[nH]1)c1cccc(Cn2nc(-c3cccnc3)ccc2=O)c1] | * | * |
| 6 | 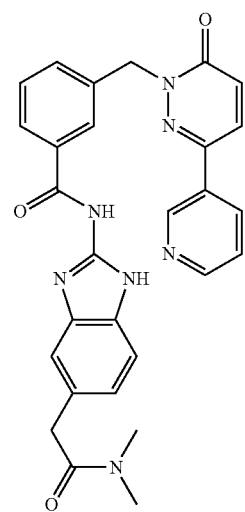 [SMILES: CN(C)C(=O)Cc1ccc2[nH]c(NC(=O)c3cccc(Cn4nc(-c5cccnc5)ccc4=O)c3)nc2c1] | * | * |
| 7 | 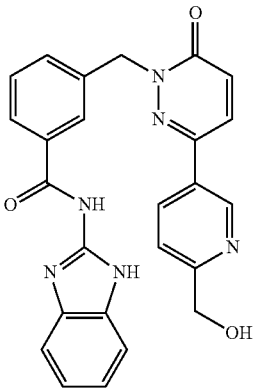 [SMILES: O=C(Nc1nc2ccccc2[nH]1)c1cccc(Cn2nc(-c3ccc(CO)nc3)ccc2=O)c1] | nd | *** |
| 8 | 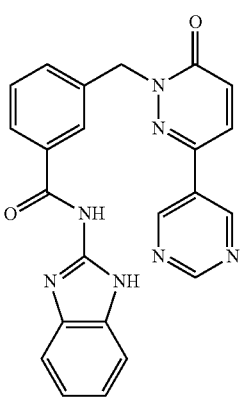 [SMILES: O=C(Nc1nc2ccccc2[nH]1)c1cccc(Cn2nc(-c3cncnc3)ccc2=O)c1] |  |  |
| 9 | 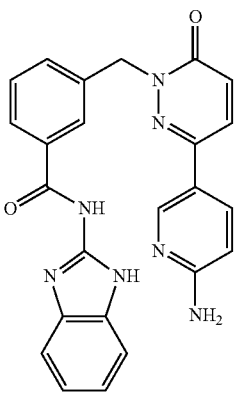 [SMILES: Nc1ccc(-c2ccc(=O)n(Cc3cccc(C(=O)Nc4nc5ccccc5[nH]4)c3)n2)cn1] | * | * |
| 10 | 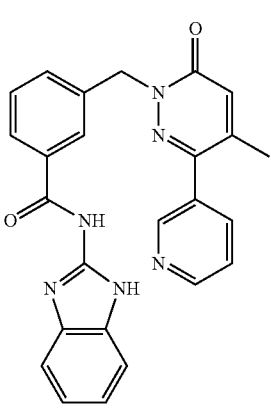 [SMILES: Cc1cc(=O)n(Cc2cccc(C(=O)Nc3nc4ccccc4[nH]3)c2)nc1-c1cccnc1] | ** | nd |

-continued
| Example | Compound | IC$_{50}$ IRAK1 | IC$_{50}$ IRAK4 |
|---|---|---|---|
| 11 | 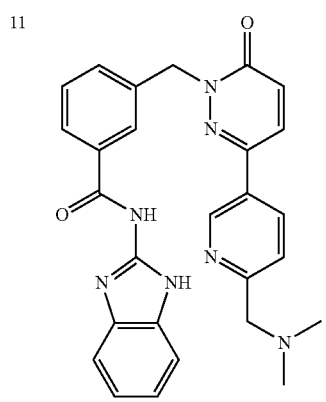 | * | * |
| 12 | 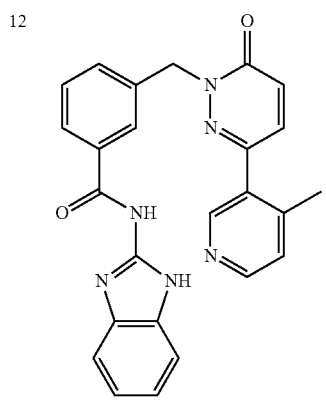 | * |  |
| 13 | 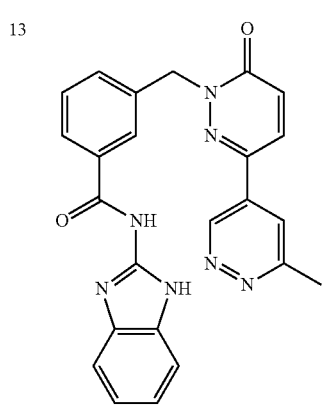 |  |  |
-continued
| Example | Compound | IC$_{50}$ IRAK1 | IC$_{50}$ IRAK4 |
|---|---|---|---|
| 14 | 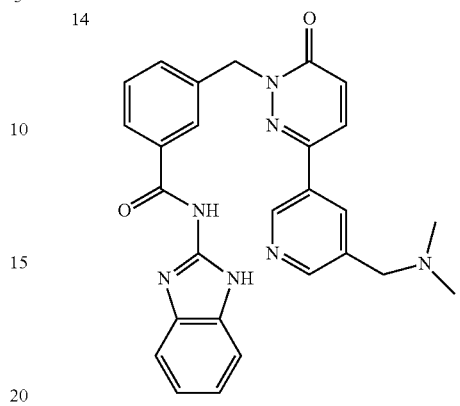 | nd | * |
| 15 | 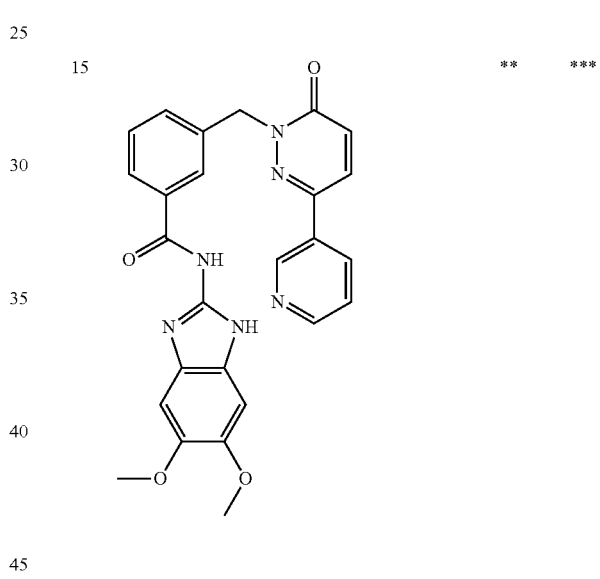 |  | * |
| 16 | 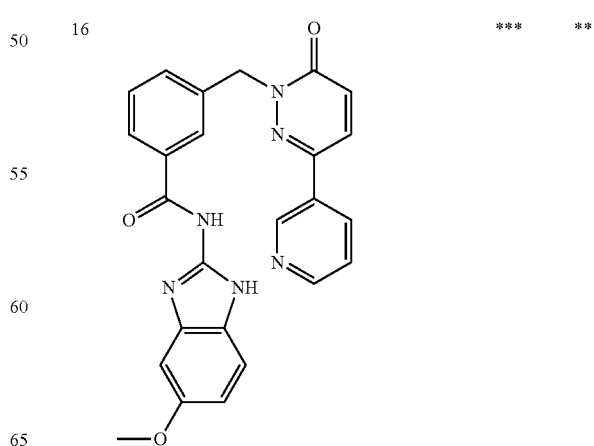 | * |  |

| Example | Compound | IC₅₀ IRAK1 | IC₅₀ IRAK4 |
|---|---|---|---|
| 17 | | *** | *** |

*: 1 µM < IC₅₀ < 5 µM
**: 0.1 µM < IC₅₀ < 1 µM
***: IC₅₀ < 0.1 µM
n.d: not determined The following abbreviations refer to the abbreviations used below:

Ac (acetyl), BINAP (2,2'-bis(disphenylphosphino)-1,1'-binaphthalene), dba (dibenzylidene acetone), Bu (Butyl), tBu (tert-Butyl), DCE (dichloroethane), DCM (Dichloromethane), DIEA (di-isopropyl ethylamine), DMA (dimethyl acetamide), DMSO (Dimethyl Sulfoxide), DMF (N,N-Dimethylformamide), Dppf (1,1'-bis (diphenyl phosphine ferrocene)), EtOAc (Ethyl acetate), EtOH (Ethanol), g (gram), cHex (Cyclohexane), HATU (N-[(Dimethylamino)(3H-[1,2,3]triazolo[4,5-b]pyridin-3-yloxy)methylene]-N-methylmethanaminiumhexafluoro phosphate), HBTU (N,N,N',N'-Tetramethyl-O-(1H-benzotriazol-1-yl)uronium hexafluorophosphate), HPLC (High Performance Liquid Chromatography), hr (hour), LC (Liquid Chromatography), LDA (lithium diisopropyl amine), LiHMDS (lithium bis (trimethylsilyl)amide), MHz (Megahertz), MeOH (Methanol), min (minute), mL (milliliter), mmol (millimole), mM (millimolar), mp (melting point), MS (Mass Spectrometry), MW (microwave), NMM (N-methylmorpholine), NMP (N-methylpyrolidine), NMR (Nuclear Magnetic Resonance), O/N (overnight), PBS (Phosphate Buffered Saline), PPh₃ (triphenyiphosphine), RT (room temperature), TEA (Triethyl amine), TFA (Trifluoroacetic acid), THF (Tetrahydrofuran), TLC (Thin Layer Chromatography), oTol (ortho-tolyl), T3P (Propylphosphonic anhydride), UV (Ultraviolet).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Depending on the nature of $R^1$, $R^a$, $R^b$, X, Y and Z different synthetic strategies may be selected for the synthesis of compounds of Formula (I). In the process illustrated in the following schemes, $R^1$, $R^a$, $R^b$, X, Y and Z are as above defined in the description unless otherwise mentioned.

Compounds of formula (I) can be prepared by coupling of a carboxylic acid compound of general formula (II) wherein A is H, Li, Na or K and an amino-benzimidazole of general formula (III) wherein $R^1$ and $R^b$ are as above defined as outlined in scheme 1. General protocols for such reaction are given below in the examples, using conditions and methods well known to those skilled in the art. Standard coupling agent, such as HBTU, EDC, T3P or isobutyl chloroformate can be used in the presence or not of an additive such as HOBt and a base such as DIEA, TEA or NMM in a suitable solvent such as DMF, Acetonitrile, THF or DCM at a temperature rising from about 0° C. to 50° C. Alternatively, a carboxylic acid derivative (such as acyl chloride) can be coupled with the amino-benzimidazole, using conditions and methods well known to those skilled in the art, in the presence of a base such as pyridine or DIEA in a suitable solvent such as toluene, DCM, THF or DMF, at a temperature rising from about 0° C. to RT, preferably at RT, for a few hours.

Scheme 1

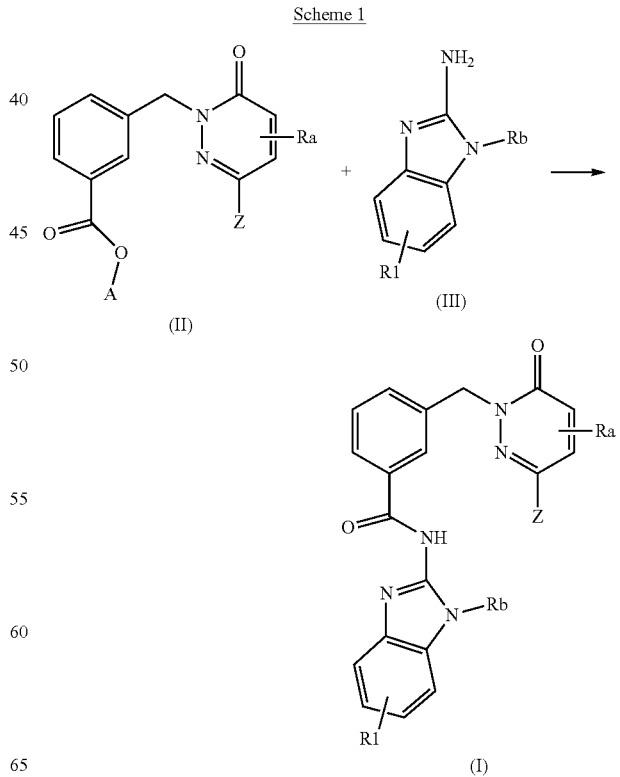

Compounds of formula (II) wherein A is H or Li, Na or K and R$^a$ and Z are as above defined can be prepared in two steps by Suzuki-Miyura coupling reaction between a pyridazinone of general formula (VI) wherein L$_1$ is halogen or a trifluoromethanesulfonate group and R is an alkyl group and a boronic acid or ester of Formula (V) wherein R is an alkyl group to give an ester of general formula (IV) wherein R is an alkyl group followed by an hydrolysis of the ester (IV) into the acid or acid salt (II) as outlined in Scheme 2. General protocols for the Suzuki-Miyura coupling reaction are given below in the Examples, using conditions and methods well known to those skilled in the art to perform such coupling (see for example Miyaura, N.; Suzuki, A. Chem. Rev. 1995, 95, 2457; Takahiro I. and Toshiaki M., Tetrahedron Lett. 2005, 46, 3573-3577). In a typical procedure, an pyridazinone of general formula (VI) and a boronic acid or ester of Formula (V) are heated in a suitable solvent, such as THF, toluene, DMF or dioxane, in the presence or absence of water as a co-solvent, in the presence of a base, such as Cs$_2$CO$_3$, Na$_2$CO$_3$, K$_2$CO$_3$, CsF, and with an appropriate catalyst such as but not limited to dichlorobis(triphenylphosphine)palladium(II), Pd(PPh$_3$)$_4$ or 1,1'-bis(diphenylphosphino)ferrocenedichloro palladium(II), Pd(OAc)$_2$, Pd$_2$(dba)$_3$, Pd(Cl)$_2$(PPh$_3$)$_2$ or Pd/C in the presence or absence of an additional ligand, such as but not limited to P(tBu)$_3$, P(oTol)$_3$, PPh$_3$, BINAP. This coupling reaction can be carried out at a temperature between about 20° C. to about 150° C., preferably at about 120° C., for a few minutes to a few hours, possibly under microwave irradiation. Hydrolysis of the ester (IV) can be performed, for example, using HCl, H$_2$SO$_4$, or using LiOH, NaOH or KOH in water, water/THF, water/THF/ethanol or water/dioxane, at temperatures between 0 and 100° C. Acid or salt form is obtained depending on the reaction treatment selected (basic or acidic conditions).

Scheme 2

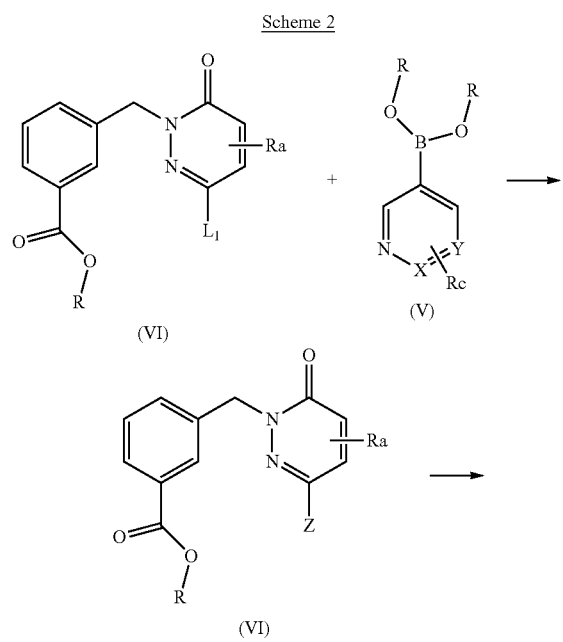

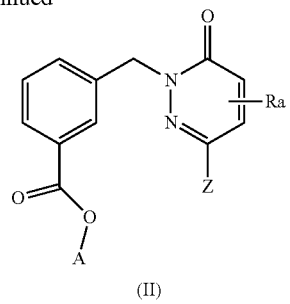

(II)

Aminobenzimidazoles of general formula (III) can be obtained from commercial sources or can be synthesized following procedures well known to those skilled in the art such as but not limited to those described in *J. Org. Chem.* 1977, 42, 542 or *Bioorganic & Medicinal Chemistry Letters* 2006, 16, 2842-2845.

Compounds of formula (VI) wherein R$^a$, L$_1$ and R are as above defined can be prepared by alkylation of a pyridazinone of general formula (VIII) wherein R$^a$ and L1 are as above defined with a compound of general formula (VII) wherein R is as above define and L$_2$ is a leaving group such as bromine, chlorine, iodine, an alkylsulfonate or any other suitable leaving group known to those skilled in the art or an OH group as outline in scheme 3. General protocols for such transformation are given below in the Examples, using conditions and methods well known to those skilled in the art. In a typical procedure, a compound of Formula (VII) wherein L2 is a leaving group is treated with a base, such as but not limited to NaH, K$_2$CO$_3$, Cs$_2$CO$_3$, LDA, LiHMDS, preferably NaH, and with a pyridazinone of Formula (VIII), in a suitable solvent like THF, dioxane, DMF, DMA, at a temperature between −20° C. to about 150° C., for a time between a few minutes to a few hours. Alternatively, Compounds of formula (VI) wherein R$^a$, L$_1$ and R are as above defined can be obtained by reaction of a compound of Formula (VII) wherein L2 is an OH group with a pyridazinone of Formula (VIII) using conditions well known to those skilled in the art for a Mitsunobu reaction (see for example Hughes, D. L. *Organic Reactions (New York)*, 1992, 42, 335-656; Reynolds, A. J.; Kassiou, M. *Current Organic Chemistry,* 2009, 13 (16); 1610-1632). Typically, the reaction takes place in the presence of a phosphine, such as but not limited to P(tBu)$_3$, PPBu$_3$, P(oTol)$_3$, PPh$_3$, in the presence of an azadicarboxylate, such as but not limited to diethylazadicarboxylate, diisopropylazadicarboxylate, Tetramethylazodicarboxamide, in a solvent such as THF, dioxane, DCM, DCE, at a temperature between −20° C. to about 150° C., preferably at room temperature, for a time between a few minutes to a few hours.

Scheme 3

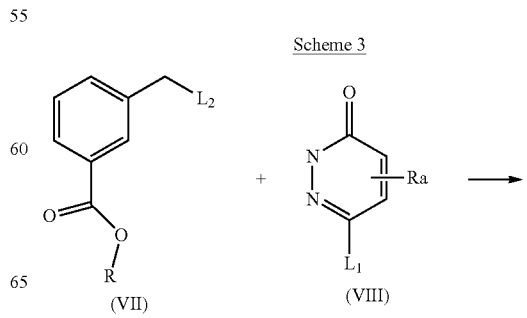

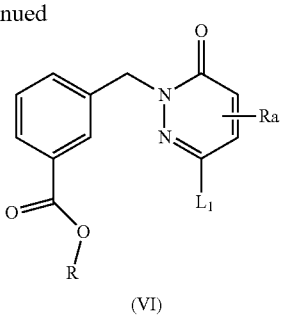

(VI)

Alternatively, compound of general formula (I) can be prepared using similar chemical steps, but in a different order such as outlined in scheme 4. After hydrolysis of compound of general formula (VI) into acid or acid salt of general formula (X), a coupling with aminobenzimidazole of general formula (II) can afford pyridazinone of general formula (XI) which can be finally reacted with a boronic acid or ester of general formula (V) through a Suzuki-Miyura coupling reaction to give compound of general formula (I). General protocols for such transformations are given below in the Examples, using conditions and methods well known to those skilled in the art. Typical conditions for those transformations are the same as above described.

Compounds of this invention can be isolated in association with solvent molecules by crystallization from an appropriate solvent or by evaporation of an appropriate solvent.

The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of an alkali or earth alkali salt (such as sodium ethylhexanoate, magnesium oleate), employing a solvent in which the desired alkali or earth alkali salt of the compounds of formula (I) precipitates, or can be otherwise isolated by concentration and addition of a non-solvent.

Both types of salts may be formed or interconverted using ion-exchange resin techniques.

Depending on the conditions used, the reaction times are generally between a few minutes and 14 days. The reaction temperature is between about −30° C. and about 140° C., Scheme 4

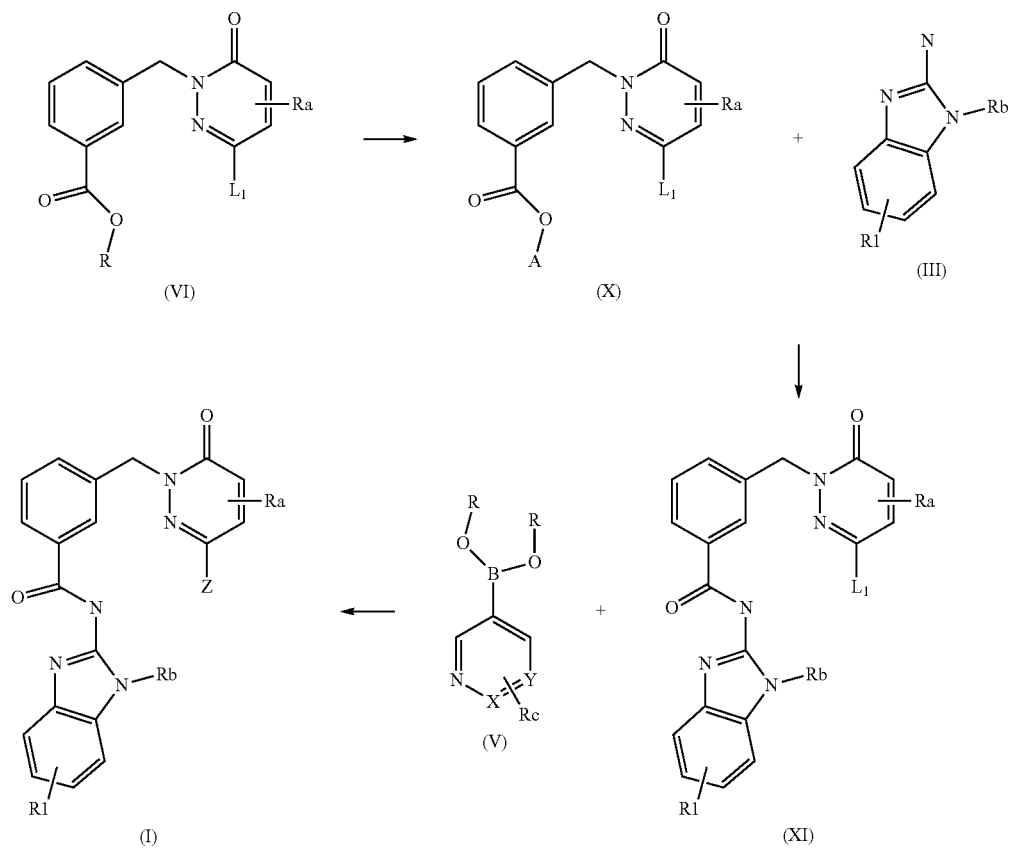

normally between −10° C. and 90° C., in particular between about 0° C. and 70° C. The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called pro¬ drug compounds.

The term "prodrug derivatives" is taken to mean compounds of the formula I which have been modified with, for example, alkyl or acyl groups, sugars or oligopeptides and which are rapidly cleaved in the organism to form the active compounds. Preferably "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995). The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medics-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I), and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I), and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels. Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base. Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a IRAK related disorder, comprising administering to said subject an effective amount of a compound of formula I and related formulae. The present invention preferably relates to a method, wherein the IRAK associated disorder is an autoimmune disorder or condition associated with an overactive immune response or cancer. The present invention furthermore relates to a method of treating a subject suffering from an immunoregulatory abnomality, comprising administering to said subject a compound of formula (1), and related formulae in an amount that is effective for treating said immunoregulatory abnormality.The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

Preferably, disorders associated with IRAK are selected from Rheumatoid Arthritis Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-I Receptor Antagonist), Alzheimer's disease, Parkinson's disease, Cancer.

Preferred compounds of formula (I), and related formulae exhibit a IC50 for the binding to IRAK of less than about 5 µM, preferably less than about 1 µM and even more preferably less than about 0.100 µM.

Experimental Part

In the following the present invention shall be illustrated by means of some examples, which are not construed to be viewed as limiting the scope of the invention.

General:

The HPLC data provided in the examples described below were obtained as followed.

Method A: Column Waters Xbridge™ C8 50 mm×4.6 mm at a flow of 2 mL/min; 8 min gradient $H_2O:CH_3CN:TFA$ from 100:0:0.1% to 0:100:0.05%. UV detection: max plot or specified wave lengh.

The LC/MS data provided in the examples described below were obtained as followed:

LC:

Method A: Column Waters Xbridge™ C8 50 mm×4.6 mm at a flow of 2 mL/min; 8 min gradient $H_2O:CH_3CN:TFA$ from 100:0:0.1% to 0:100:0.05%

Method B: Column Waters Xbridge™ C8 50 mm×4.6 mm at a flow of 1 mL/min; 8 min gradient $H_2O:CH_3CN:NH_4HCO_3$ from 100:0:0.1% to 0:100:0.05%

UV detection: max plot or specified wave lengh.

Mass spectrum: MS Waters ZMD (ESI).

The NMR data provided in the examples described below were obtained using a Bruker AV-400 MHz.

The compounds of invention have been named according to the standards used in the program Autonom.

The compounds according to formula (I) can be prepared from readily available starting materials by several synthetic approaches, using both solution-phase and solid-phase chemistry protocols or mixed solution and solid phase protocols. Examples of synthetic pathways are described below in the examples. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich or Sigma or ABCR unless otherwise reported.

Intermediate 1: Lithium 3-(6-oxo-3-pyridin-3-yl-6H-pyridazin-1-ylmethyl)-benzoate Step 1: Formation of 3-(6-Oxo-3-pyridin-3-yl-6H-pyridazin-1-ylmethyl)-benzoic acid methyl ester

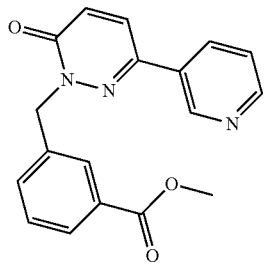 [SMILES: COC(=O)c1cccc(Cn2nc(-c3cccnc3)ccc2=O)c1]

Tribromophosphane (1.7 g, 6.6 mmol) was added to a solution of 3-hydroxymethyl-benzoic acid methyl ester (1 g, 6.0 mmol) in diethyl ether (20 mL) at 0° C. The reaction mixture was allowed to warm to RT and stirred for 2 h. It was then treated with water. The aqueous phase was basified with saturated $NaHCO_3$ solution (15 mL) and extracted with dichloromethane. Combined organic phases were dried over anhydrous $Na_2SO_4$, filtered and concentrated to give 3-bromomethyl-benzoic acid methyl ester which was dissolved in NMP. 6-pyridin-3-yl-2H-pyridazin-3-one (1.1 g, 6.5 mmol) and cesium carbonate (2.1 g, 6.5 mmol) were then added to this solution and the reaction mixture was stirred at RT for 12 h. It was treated with water, the aqueous phase was extracted with ethyl acetate (3×15 mL) and combined organic phases were dried over anhydrous $Na_2SO_4$, filtered, and concentrated under reduced pressure. Purification by flash chromatography on silica afforded the title product as a yellow solid (0.8 g, 57%). LC/MS: (Method A) 322.2 (M+H), RT. 2.51 min, 66.4% (Max).

Step 2: Formation of Lithium 3-(6-oxo-3-pyridin-3-yl-6H-pyridazin-1-ylmethyl)-benzoate

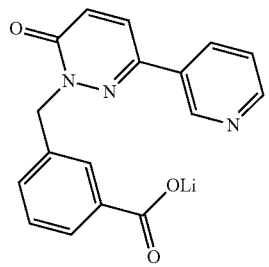

A solution of Lithium hydroxide monohydrate (0.35 g, 8.7 mmol) and 3-(6-oxo-3-pyridin-3-yl-6H-pyridazin-1-ylmethyl)-benzoic acid methyl ester (1.4 g, 4.35 mmol) in THF:water (1:2, 10 mL) was stirred at RT for 12 h. The reaction mixture was concentrated, and azeotroped with toluene to afford the title compound as a yellow solid (0.5 g, 52%). $^1$HNMR (400 MHz, DMSO-d6): δ 13.01 (brs, 1H), 9.09-9.08 (m, 1H), 8.65-8.63 (m, 1H), 8.27-8.24 (m, 1H), 8.15 (d, J=9.8 Hz, 1H), 7.95 (s, 1H), 7.86 (t, J=1.3 Hz, 1H), 7.63 (d, J=7.8 Hz, 1H), 7.54-7.47 (m, 2H), 7.15 (d, J=9.8 Hz, 1H), 5.41 (s, 2H). LC/MS: (Method A) 308.0 (M+H), RT. 2.0 min, 90.1% (Max).

Intermediate 2: 3-(3-Chloro-6-oxo-6H-pyridazin-1-ylmethyl)-benzoic acid methyl ester

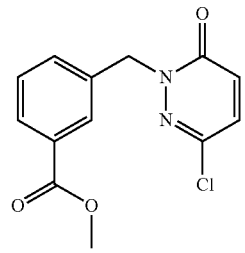 [SMILES: COC(=O)c1cccc(Cn2nc(Cl)ccc2=O)c1]

The title compound was obtained following procedure described for intermediate 1, step 1 from 3-hydroxymethyl-benzoic acid methyl ester and 6-chloro-3-yl-2H-pyridazin-3-one as an off-white solid (9.8 g, 94%). LC/MS: (Method A) 279.0 (M+H), RT. 3.7 min, 93.8% (Max), 93.9% (254 nm).

Intermediate 3: 3-(3-Chloro-6-oxo-6H-pyridazin-1-ylmethyl)-benzoic acid

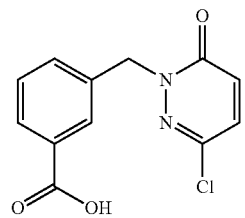 [SMILES: O=C(O)c1cccc(Cn2nc(Cl)ccc2=O)c1]

A solution of lithium hydroxide monohydrate (0.307 g, 7.5 mmol) and 3-(3-Chloro-6-oxo-6H-pyridazin-1-ylmethyl)-benzoic acid methyl ester (1.2 g, 4.30 mmol) in THF:water (2:1, 30 mL) was stirred at RT for 12 h. The reaction mixture was then concentrated, acidified with a saturated citric acid solution (15 mL) and extracted with dichloromethane (3×10 mL). The combined organic phases were washed with brine, dried over anhydrous Na$_2$SO$_4$, filtered, and concentrated to afford the title compound as an off-white solid (1.5 g, 83%). LC/MS: (Method A) 265.0 (M+H), RT. 2.9 min, 94.1% (Max).

Intermediate 4: 2-(2-amino-1H-benzo[d]imidazol-5-yl)-N,N-dimethylacetamide

Step 1: Formation of 2-(benzo[c][1,2,5]thiadiazol-5-yl)-N,N-dimethylacetamide

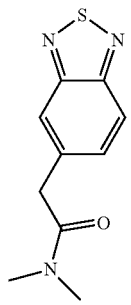

To a solution of Benzo[1,2,5]thiadiazol-5-yl-acetic acid (prepared as described in *Bioorg. Med. Chem. Lett.* (1998) p 17-22, 5 g, 25.7 mmol) in THF were added N,N-Dimethyl amine (15.4 ml, 30.8 mmol) and triethylamine (0.1 mL, 0.8 mmol) at 0° C. To this reaction mixture T$_3$P (50% w/v solution in ethyl acetate, 49 mL, 77.2 mmol) was added and stirred at room temperature for 12 h. The reaction mixture was washed with 10% sodium bicarbonate (15 mL) and extracted with dichloromethane (3×10 mL). The combined organic phases were washed with a 10% citric acid solution, dried over anhydrous Na$_2$SO$_4$, filtered and concentrated to afford the title compound as a yellow solid (3 g, 53%). $^1$H NMR (400 MHz, DMSO-d$_6$): δ 8.00 (d, J=9.0 Hz, 1H), 7.88 (d, J=0.7 Hz, 1H), 7.58-7.56 (m, 1H), 3.93 (s, 2H), 3.06 (s, 3H), 2.85 (s, 3H). LC/MS: (Method A) 222.0 (M+H), RT. 2.4 min, 96.1% (Max), 96.5% (220 nm).

Step 2: Formation of 2-(3,4-diaminophenyl)-N,N-dimethylacetamide

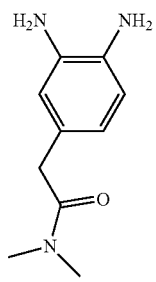

Raney nickel (9 g, 40.5 mmol) was added to a solution of 2-(benzo[c][1,2,5]thiadiazol-5-yl)-N,N-dimethylacetamide (3 g, 13.5 mmol) in methanol (100 mL). The reaction mixture was then heated at 45° C. for 12 h in an autoclave. It was then filtered through a celite pad and the filtrate was concentrated under reduced pressure to give the title compound as a brown solid (2.0 g, 76%). $^1$H NMR (400 MHz, DMSO-d$_6$): δ 6.72-6.35 (m, 2H), 6.29-6.16 (m, 1H), 4.39 (brs, 2H), 4.29 (brs, 2H), 3.32 (s, 2H), 2.92 (s, 3H), 2.78 (s, 3H). LC/MS: (Method B) 194.3 (M+H), RT. 2.4 min, 92.9% (Max).

Step 3: Formation of 2-(2-amino-1H-benzo[d]imidazol-5-yl)-N,N-dimethylacetamide

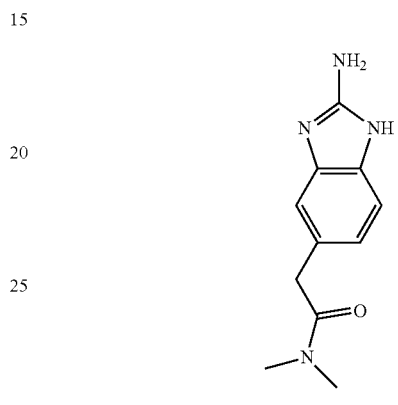

A solution of 2-(3,4-diaminophenyl)-N,N-dimethylacetamide (3.0 g, 15.5 mmol) in ethanol (15 mL) was added over a period of 30 min to a stirred solution of cyanogen bromide (1.8 g, 17.0 mmol) in water (100 mL). The reaction mixture was stirred at RT for 20 h. Ethanol was removed under reduced pressure. The resulting aqueous phase was basified with a saturated solution of NaHCO$_3$ and extracted with ethyl acetate. The combined organic phases were dried over anhydrous Na$_2$SO$_4$, filtered and concentrated to give the title compound as a brown solid (1.0 g, 45%). $^1$H NMR (400 MHz, DMSO-d$_6$): δ 10.58 (s, 1H), 6.99-6.95 (m, 1H), 6.95-6.90 (m, 1H), 6.70 (d, J=16.3 Hz, 1H), 6.05 (brs, 2H), 3.62 (s, 2H), 2.95 (s, 3H), 2.81 (s, 3H). LC/MS: (Method A) 219.2 (M+H), RT. 1.5 min, 97.0% (Max), 97.0% (220 nm).

Intermediate 5: 3-[3-(6-Hydroxymethyl-pyridin-3-yl)-6-oxo-6H-pyridazin-1-ylmethyl]-benzoic acid Step 1: Formation of 3-[3-(6-Hydroxymethyl-pyridin-3-yl)-6-oxo-6H-pyridazin-1-ylmethyl]-benzoic acid methyl ester

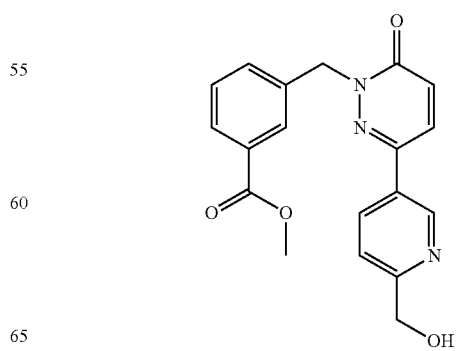

A mixture of 3-(3-chloro-6-oxo-6H-pyridazin-1-ylmethyl)-benzoic acid methyl ester (0.5 g, 1.79 mmol) and [5-(4,4,5,5-tetramethyl-1,3,2-dioxaborolan-2-yl)-2-pyridyl]methanol (0.831 g, 3.53 mmol) in DMF/H$_2$O (9 mL/1 mL) was degassed under N$_2$ atmosphere for 10 min, Na$_2$CO$_3$ (2.6 mL, 2 M solution, 5.39 mmol) was added to the above followed by bis(triphenylphosphine)palladium(II) dichloride (0.063 g, 0.089 mmol). The reaction mixture was then heated at 100° C. for 3 h, diluted with water and extracted with EtOAc. Combined organic layers were then washed with water, brine, dried over anhydrous Na$_2$SO$_4$, filtrated and concentrated. Purification of the crude by flash chromatography on silica (n-Hexane: EtOAc, 80:20) afforded the title compound as a yellow solid (380 mg, 52%). LC/MS: (Method A) 352.0 (M+H), RT. 2.4 min, 94.8% (Max).

Step 2: Formation of 3-[3-(6-Hydroxymethyl-pyridin-3-yl)-6-oxo-6H-pyridazin-1-ylmethyl]-benzoic acid

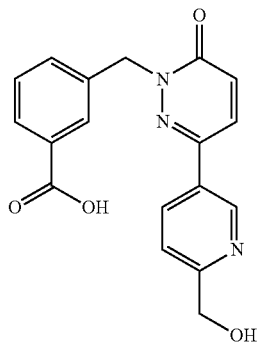 [SMILES: O=C(O)c1cccc(Cn2nc(-c3ccc(CO)nc3)ccc2=O)c1]

The title compound was obtained following procedure described for intermediate 3 from 3-[3-(6-Hydroxymethyl-pyridin-3-yl)-6-oxo-6H-pyridazin-1-ylmethyl]-benzoic acid methyl ester as an off-white solid (230 mg, 63%). LC/MS: (Method A) 338.2 (M+H), RT. 1.9 min, 95.1% (Max), 93.4% (254 nm).

Intermediate 6: N-(1H-Benzoimidazol-2-yl)-3-(3-chloro-6-oxo-6H-pyridazin-1-ylmethyl)-benzamide

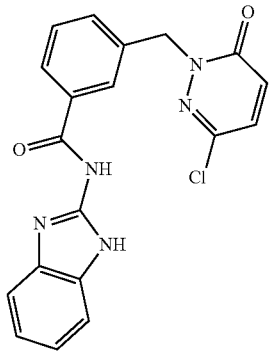 [SMILES: O=C(Nc1nc2ccccc2[nH]1)c1cccc(Cn2nc(Cl)ccc2=O)c1]

A solution of 1H-benzoimidazol-2-ylamine (0.55 g, 4.17 mmol), 3-(3-Chloro-6-oxo-6H-pyridazin-1-ylmethyl)-benzoic acid (0.85 g, 3.21 mmol), N-methyl morpholine (0.4 mL, 3.38 mmol), 1-hydroxy benzotriazole (47 mg, 3.53 mmol) and HBTU (1.4 g, 3.69 mmol) in DMF (5 mL) was stirred at RT for 12 h. The reaction mixture was then quenched with water and concentrated under reduced pressure. The crude product was purified by flash chromatography on silica to give the title compound as a yellow solid (0.7 g, 58%). $^1$H NMR (400 MHz, DMSO-d$_6$): δ 12.31 (s, 2H), 8.07 (dd, J$_1$=2.0 Hz, 9.8 Hz, 1H), 8.03 (s, 1H), 7.61 (d, J=9.8 Hz, 1H), 7.51 (d, J=6.7 Hz, 2H), 7.44-7.42 (m, 2H), 7.14-7.11 (m, 3H), 5.28 (s, 2H). LC/MS: (Method A) 380.0 (M+H), RT. 3.0 min, 98.8% (Max).

Intermediate 7: 3-(3-Chloro-4-methyl-6-oxo-6H-pyridazin-1-ylmethyl)-benzoic acid methyl ester

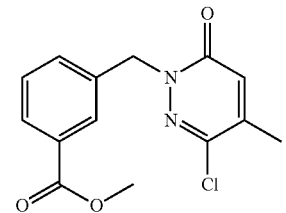 [SMILES: COC(=O)c1cccc(Cn2nc(Cl)c(C)cc2=O)c1]

A mixture of 3-Bromomethyl-benzoic acid methyl ester (3.0 g, 13.1 mmol), 6-Chloro-5-methyl-2H-pyridazin-3-one (1.9 g, 13.1 mmol) and cesium carbonate (4.25 g, 13.1 mmol) in N-methyl pyrrolidine (15 mL) was stirred at RT for 14 h. The reaction mixture was then poured into ice and extracted with DCM (3 times). Combined organic phases were washed with brine, dried over Na$_2$SO$_4$, filtered and concentrated. Purification by flash column chromatography on silica afforded the title compound as a brown solid (1.5 g, 39%). LC/MS: (Method A) 293.0 (M+H), RT. 4.4 min, 90.1% (Max). $^1$H NMR (400 MHz, DMSO-d$_6$): δ 7.88 (dd, J=1.2, 7.7 Hz, 2H), 7.57 (t, J=6.4 Hz, 1H), 7.50 (t, J=7.7 Hz, 1H), 7.04 (d, J=1.2 Hz, 1H), 5.25 (s, 2H), 3.84 (s, 3H), 2.19 (s, 3H).

Intermediate 8: Lithium 3-(4-Methyl-6-oxo-3-pyridin-3-yl-6H-pyridazin-1-ylmethyl)-benzoate Step 1: Formation of 3-(4-Methyl-6-oxo-3-pyridin-3-yl-6H-pyridazin-1-ylmethyl)-benzoic acid methyl ester A mixture of 3-(3-Chloro-4-methyl-6-oxo-6H-pyridazin-1-ylmethyl)-benzoic acid methyl ester (1.5 g, 5.13 mmol) and pyridine 3-boronic acid (0.94 g, 7.7 mmol) in DMF/H$_2$O (9:1; 30 mL) was degassed under N$_2$ atmosphere for 10 min, Na$_2$CO$_3$ (7.7 mL, 15.4 mmol) was added to the above followed by bis(triphenylphosphine)palladium(II) dichloride (0.18 g, 0.25 mmol). The reaction mixture was then heated at 100° C. for 4 h and filtered through a celite pad. Celite pad was washed with dichloromethane/methanol and the filtrate was concentrated under reduced pressure. Purification of the crude by flash chromatography on silica afforded the title compound as a brown solid (1 g, 59%). $^1$H NMR (400 MHz, DMSO-d$_6$): δ 8.69-8.64 (m, 2H), 7.98-7.95 (m, 2H), 7.95-7.86 (m, 1H), 7.62-7.60 (m, 1H), 7.52-7.48 (m, 2H), 6.98 (d, J=1.2 Hz, 1H), 5.35 (s, 2H), 3.84 (s, 3H), 2.15 (s, 3H). LC/MS: (Method A) 336.2 (M+H), RT. 2.5 min, 89.5% (Max), 89.1% (254 nm).

Step 2: Formation of Lithium 3-(4-Methyl-6-oxo-3-pyridin-3-yl-6H-pyridazin-1-ylmethyl)-benzoate

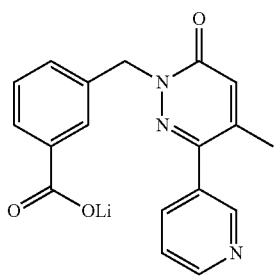

The title compound was obtained following procedure described for Intermediate 1, step 2 from 3-(4-Methyl-6-oxo-3-pyridin-3-yl-6H-pyridazin-1-ylmethyl)-benzoic acid methyl ester as a brown solid (0.5 g, 65%). $^1$H NMR (400 MHz, DMSO-d$_6$): δ 8.69-8.64 (m, 2H), 7.98-7.95 (m, 1H), 7.80-7.74 (m, 2H), 7.51-7.47 (m, 1H), 7.24-7.18 (m, 2H), 6.97 (d, J=1.2 Hz, 1H), 5.27 (s, 2H), 2.16 (s, 3H). LC/MS: (Method A) 322.2 (M+H), RT. 2.0 min, 88.7% (Max), 90.2% (254 nm).

Intermediate 9: Dimethyl-[5-(4,4,5,5-tetramethyl-[1,3,2]dioxaborolan-2-yl)-pyridin-2-ylmethyl]-amine

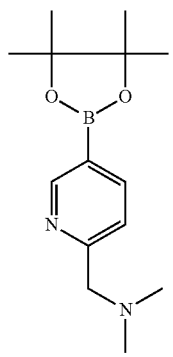

A mixture of (5-Bromo-pyridin-2-ylmethyl)-dimethyl-amine (purchased from rare Chemicals, 3 g, 13.94 mmol) and bis(pinacolato)diboron (3.9 g, 15.34 mmol) in dioxane (40 mL) was degassed under N$_2$ atmosphere for 10 min, potassium acetate (2.8 g, 27.89 mmol) was added to the above followed by 1,1'-Bis(diphenylphosphino)ferrocene] dichloropalladium(II). CH$_2$Cl$_2$ (0.50 g, 0.69 mmol). The reaction mixture was then heated at 60° C. for 14 h and filtered through a celite pad. Celite pad was washed with dichloromethane/methanol and the filtrate was concentrated under reduced pressure to give the title compound a brown gum (1.5 g, 41%). LC/MS: (Method A) 181.0 (M-82, boronic acid), RT. 0.42 min, 97.09% (Max).

EXAMPLE 1

2,2-Dimethyl-propionic acid 2-[3-(6-oxo-3-pyridin-3-yl-6H-pyridazin-1-ylmethyl)-benzoylamino]-1H-benzoimidazol-5-yl ester

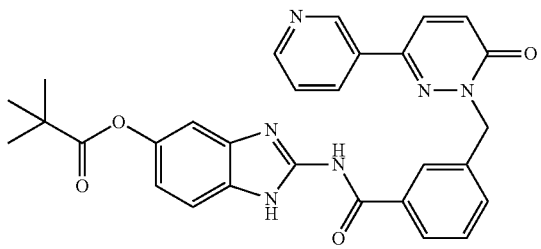 [SMILES: CC(C)(C)C(=O)Oc1ccc2[nH]c(NC(=O)c3cccc(Cn4nc(-c5cccnc5)ccc4=O)c3)nc2c1]

A solution of 2,2-dimethyl-propionic acid 2-amino-1H-benzoimidazol-5-yl ester (purchased from Ambinter Stock Screening Collection, 0.15 g, 0.6 mmol), lithium 3-(6-Oxo-3-pyridin-3-yl-6H-pyridazin-1-ylmethyl)benzoate (0.1 g, 0.3 mmol), N-methyl morpholine (0.1 mL, 0.9 mmol), 1-hydroxy benzotriazole (80 mg, 0.6 mmol) and HBTU (200 mg, 0.6 mmol) in DMF (5 mL) was stirred at room temperature for 12 h. The reaction mixture was then diluted with a 10% sodium bicarbonate solution (15 mL) and extracted with dichloromethane (3×10 mL). The combined organic phases were washed with a 10% citric acid solution, dried over anhydrous Na$_2$SO$_4$, filtered and concentrated. The resulting solid was stirred with methanol (5 mL), filtered and dried under vacuum to give the title compound as a brown solid (29 mg, 10%). $^1$HNMR (400 MHz, DMSO-d6): δ 12.37 (brs, 2H), 9.12 (t, J=1.6 Hz, 1H), 8.65 (dd, J=4.8, 1.6 Hz, 1H), 8.28 (dt, J=4.9, 2.3 Hz, 1H), 8.17-8.12 (m, 2H), 8.07 (d, J=7.8 Hz, 1H), 7.62 (d, J=7.6 Hz, 1H), 7.54-7.49 (m, 2H), 7.42 (d, J=8.4 Hz, 1H), 7.18-7.13 (m, 2H), 6.81 (dd, J=8.6, 1.9 Hz, 1H), 5.44 (s, 2H), 1.31 (s, 9H). LC/MS: (Method A) 523.3 (M+H), RT. 3.2 min, 91.9% (Max), 90.3% (254 nm). HPLC: (Method A) RT 3.5 min, 92.1% (Max), 93.1% (254 nm).

EXAMPLE 2

N-(1H-Benzoimidazol-2-yl)-3-(6-oxo-3-pyridin-3-yl-6H-pyridazin-1-ylmethyl)-benzamide

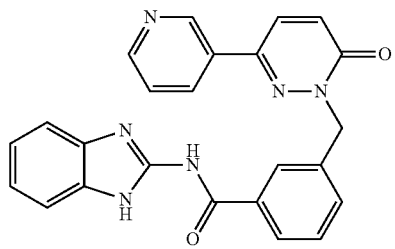 [SMILES: O=C(Nc1nc2ccccc2[nH]1)c1cccc(Cn2nc(-c3cccnc3)ccc2=O)c1]

The title compound was obtained following procedure described for example 1 from Lithium 3-(6-oxo-3-pyridin- 3-yl-6H-pyridazin-1-ylmethyl)-benzoate and 1H-benzimidazol-2-amine as a brown solid (135 mg, 12%). ¹HNMR (400 MHz, DMSO-d6): δ 12.39 (brs, 2H), 9.12 (t, J=1.7 Hz, 1H), 8.65 (dd, J=4.76, 1.6 Hz, 1H), 8.29-8.26 (m, 1H), 8.17-8.14 (m, 2H), 8.07 (d, J=7.8 Hz, 1H), 7.60 (d, J=7.5 Hz, 1H), 7.54-7.50 (m, 2H), 7.44-7.42 (m, 2H), 7.15-7.11 (m, 3H), 5.44 (s, 2H). LC/MS: (Method A) 423.0 (M+H), RT. 2.4 min, 97.8% (Max), 98.3% (254 nm). HPLC: (Method A) RT 2.4 min, 98.3% (Max), 97.8% (254 nm).

EXAMPLE 3

N-(1-Methyl-1H-benzoimidazol-2-yl)-3-(6-oxo-3-pyridin-3-yl-6H-pyridazin-1-ylmethyl)-benzamide

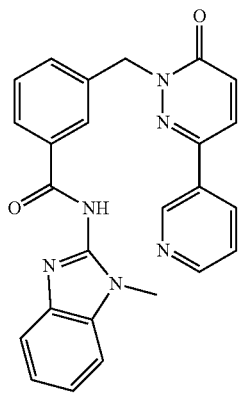 [SMILES: Cn1c(NC(=O)c2cccc(Cn3nc(-c4cccnc4)ccc3=O)c2)nc2ccccc21]

The title compound was obtained following procedure described for example 1 from Lithium 3-(6-oxo-3-pyridin-3-yl-6H-pyridazin-1-ylmethyl)-benzoate and 1-methylbenzimidazol-2-amine as an off-white solid (11 mg, 18%). ¹HNMR (400 MHz, DMSO-d6): δ 12.70 (s, 1H), 9.13 (d, J=1.8 Hz, 1H), 8.65 (dd, J=4.7, 1.5 Hz, 1H), 8.31-8.26 (m, 2H), 8.18-8.16 (m, 2H), 7.55-7.43 (m, 5H), 7.27-7.20 (m, 3H), 5.44 (s, 2H), 3.64 (s, 3H). LC/MS: (Method A) 437.2 (M+H), RT. 2.5 min, 96.3% (Max), 96.7% (254 nm). HPLC: (Method A) RT 2.4 min, 96.1% (Max), 95.6% (254 nm).

EXAMPLE 4

2-[3-(6-Oxo-3-pyridin-3-yl-6H-pyridazin-1-ylmethyl)-benzoylamino]-1H-benzoimidazole-5-carboxylic acid methyl ester The title compound was obtained following procedure described for example 1 from Lithium 3-(6-oxo-3-pyridin-3-yl-6H-pyridazin-1-ylmethyl)-benzoate and methyl 2-amino-1H-benzimidazole-5-carboxylate (purchased from PharmaCore inc.) as a brown solid (13 mg, 19%). ¹HNMR (400 MHz, DMSO-d6): δ 12.65 (brs, 1H), 12.25 (brs, 1H), 9.12 (d, J=1.8 Hz, 1H), 8.65 (dd, J=4.7, 1.3 Hz, 1H), 8.28 (d, J=7.8 Hz, 1H), 8.17 (d, J=9.7 Hz, 1H), 8.12-7.98 (m, 3H), 7.84-7.78 (m, 1H), 7.65 (d, J=6.8 Hz, 1H), 7.55-7.51 (m, 3H), 7.17 (d, J=9.72 Hz, 1H), 5.45 (s, 2H), 3.85 (s, 3H).

LC/MS: (Method A) 481.2 (M+H), RT. 2.6 min, 94.9% (Max), 93.7% (254 nm). HPLC: (Method A) RT 2.5 min, 92.6% (Max), 92.5% (254 nm).

EXAMPLE 5

N-(5-Hydroxymethyl-1H-benzoimidazol-2-yl)-3-(6-oxo-3-pyridin-3-yl-6H-pyridazin-1-ylmethyl)-benzamide

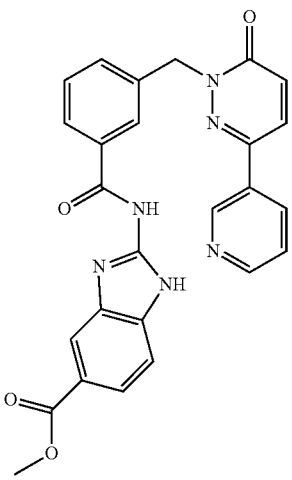 [SMILES: COC(=O)c1ccc2[nH]c(NC(=O)c3cccc(Cn4nc(-c5cccnc5)ccc4=O)c3)nc2c1]

The title compound was obtained following procedure described for example 1 from Lithium 3-(6-Oxo-3-pyridin-3-yl-6H-pyridazin-1-ylmethyl)-benzoate and (2-amino-1H-benzimidazol-5-yl)methanol (purchased from FCH Group Reagents for Synthesis) as a yellow solid (6 mg, 11%). ¹HNMR (400 MHz, DMSO-d6): δ 12.60 (brs, 1H), 9.12 (s, 1H), 8.65 (d, J=3.2 Hz, 1H), 8.28 (d, J=7.2 Hz, 1H), 8.17-8.14 (m, 2H), 8.07 (d, J=7.2 Hz, 1H), 7.61-7.48 (m, 3H), 7.40 (s, 1H), 7.36 (d, J=8.0 Hz, 1H), 7.18-7.15 (m, 2H), 5.44 (s, 2H), 5.15 (brs, 1H), 4.54 (s, 2H), 2.53 (s, 1H). LC/MS: (Method A) 453.3 (M+H), RT. 2.0 min, 94.5% (Max), 96.0% (254 nm). HPLC: (Method A) RT 2.0 min, 98.1% (Max), 97.3% (254 nm).

EXAMPLE 6

N-(5-Dimethylcarbamoylmethyl-1H-benzoimidazol-2-yl)-3-(6-oxo-3-pyridin-3-yl-6H-pyridazin-1-ylmethyl)-benzamide

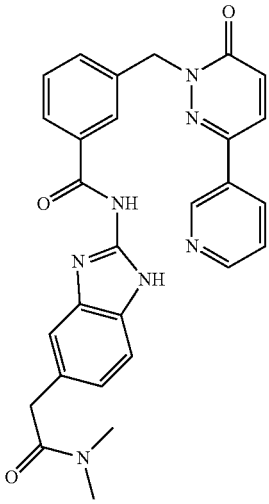 [SMILES: CN(C)C(=O)Cc1ccc2[nH]c(NC(=O)c3cccc(Cn4nc(-c5cccnc5)ccc4=O)c3)nc2c1]

The title compound was obtained following procedure described for example 1 from 3-(6-Oxo-3-pyridin-3-yl-6H-pyridazin-1-ylmethyl)-lithium benzoate and 2-(2-amino-1H-benzo[d]imidazol-5-yl)-N,N-dimethylacetamide as an off-white solid (49 mg, 19%). $^1$HNMR (400 MHz, DMSO-d6): δ 12.26 (brs, 2H), 9.11 (d, J=1.8 Hz, 1H), 8.64 (dd, J=4.7, 1.5 Hz, 1H), 8.28 (td, J=8.1, 1.9, Hz, 1H), 8.17 (s, 1H), 8.15 (s, 1H), 8.07 (d, J=7.8 Hz, 1H), 7.55-7.51 (m, 2H), 7.45 (t, J=7.7 Hz, 1H), 7.30-7.28 (m, 1H), 7.23 (s, 1H), 7.16 (d, J=9.7 Hz, 1H), 6.94-6.92 (m, 1H), 5.42 (s, 2H), 3/1 (s, 2H), 3.0 (s, 3H), 2.8 (s, 3H). LC/MS: (Method A) 508.2 (M+H), RT. 2.2 min, 97.1% (Max), 98.9% (254 nm). HPLC: (Method A) RT 2.1 min, 96.5% (Max), 95.4% (254 nm).

EXAMPLE 7

N-(1H-Benzoimidazol-2-yl)-3-[3-(6-hydroxymethyl-pyridin-3-yl)-6-oxo-6H-pyridazin-1-ylmethyl]-benzamide

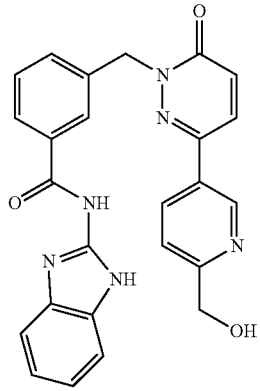 [SMILES: O=C(Nc1nc2ccccc2[nH]1)c1cccc(Cn2nc(-c3ccc(CO)nc3)ccc2=O)c1]

The title compound was obtained following procedure described for example 1 from 3-[3-(6-hydroxymethyl-pyridin-3-yl)-6-oxo-6H-pyridazin-1-ylmethyl]-benzoic acid and 1H-benzimidazol-2-amine as an off-white solid (28 mg, 12%). $^1$HNMR 400 MHz, DMSO-d6: δ 12.29 (brs, 2H), 9.02 (d, J=2.0 Hz, 1H), 8.28 (dd, J=8.2, 2.2, Hz, 1H), 8.16 (s, 1H), 8.14 (s, 1H), 8.07 (d, J=7.8 Hz, 1H), 7.61-7.59 (m, 2H), 7.50 (t, J=7.6 Hz, 1H), 7.44-7.42 (m, 2H), 7.16-7.12 (m, 3H), 5.52 (s, 1H), 5.43 (s, 2H), 4.61 (d, J=5.32 Hz, 2H). LC/MS: (Method A) 453.3 (M+H), RT. 2.2 min, 97.8% (Max), 98.2% (254 nm). HPLC: (Method A) RT 2.4 min, 98.3% (Max), 97.8% (254 nm).

EXAMPLE 8

N-(1H-Benzoimidazol-2-yl)-3-(6-oxo-3-pyrimidin-5-yl-6H-pyridazin-1-ylmethyl)-benzamide

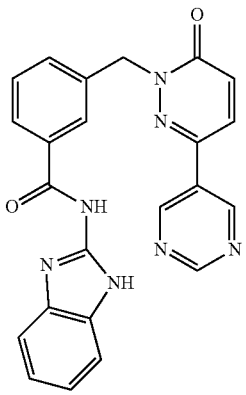 [SMILES: O=C(Nc1nc2ccccc2[nH]1)c1cccc(Cn2nc(-c3cncnc3)ccc2=O)c1]

The title compound was obtained following procedure described for intermediate 5, step 1 from N-(1H-Benzoimidazol-2-yl)-3-(3-chloro-6-oxo-6H-pyridazin-1-ylmethyl)-benzamide and 5-(4,4,5,5-tetramethyl-1,3,2-dioxaborolan-2-yl)pyrimidine as an off-white solid (12 mg, 9%). $^1$HNMR (400 MHz, DMSO-d6): δ 12.30 (brs, 2H), 9.31(s, 2H), 9.26 (s, 1H), 8.22-8.07 (m, 3H), 7.62 (s, 1H), 7.49 (t, J=6.6 Hz, 3H), 7.18 (t, J=9.6 Hz, 3H), 5.44 (s, 2H). LC/MS: (Method A) 424.2 (M+H), RT. 2.6 min, 95.6% (Max), 97.9% (254 nm). HPLC: (Method A) RT 2.6 min, 98.7% (Max), 98.4% (254 nm).

EXAMPLE 9

3-[3-(6-Amino-pyridin-3-yl)-6-oxo-6H-pyridazin-1-ylmethyl]-N-(1H-benzoimidazol-2-yl)-benzamide

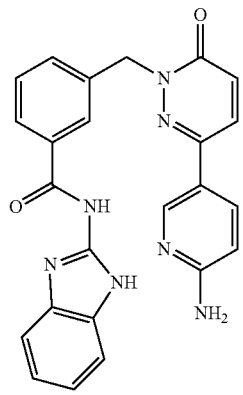

The title compound was obtained following procedure described for intermediate 5, step 1 from N-(1H-Benzoimidazol-2-yl)-3-(3-chloro-6-oxo-6H-pyridazin-1-ylmethyl)-benzamide and 5-(4,4,5,5-tetramethyl-1,3,2-dioxaborolan-2-yl)pyridin-2-amine as yellow solid (55 mg, 36%). $^1$HNMR (400 MHz, DMSO-d6): δ 12.32 (s, 2H), 8.47 (d, J=2.3 Hz, 1H), 8.10 (s, 1H), 8.06 (d, J=7.8 Hz, 1H), 8.00 (d, J=9.8 Hz, 1H), 7.88 (dd, J=8.7, 2.4 Hz, 1H), 7.56 (d, J=7.5 Hz, 1H), 7.49 (t, J=7.6 Hz, 1H), 7.44-7.42 (m, 2H), 7.14-7.12 (m, 2H), 7.04 (d, J=9.7 Hz, 1H), 6.50 (d, J=8.8 Hz, 1H), 6.39 (s, 2H), 5.36 (s, 2H). LC/MS: (Method A) 438.2 (M+H), RT. 2.3 min, 94.9% (Max), 98.3% (254 nm). HPLC: (Method A) RT 2.5 min, 99.5% (Max), 99.2% (254 nm).

EXAMPLE 10

N-(1H-benzo[d]imidazol-2-yl)-3-(2-cyano-5-(pyridin-3-yl)phenoxy)benzamide

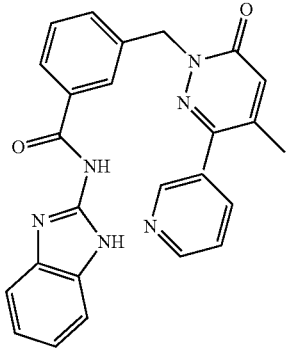 [SMILES: Cc1cc(=O)n(Cc2cccc(C(=O)Nc3nc4ccccc4[nH]3)c2)nc1-c1cccnc1]

The title compound was obtained following procedure described for example 1 from Lithium 3-(4-Methyl-6-oxo-3-pyridin-3-yl-6H-pyridazin-1-ylmethyl)-benzoate and 1H-benzimidazol-2-amine with an additional purification step by flash chromatography on silica as an off-white solid (26 mg, 20%). $^1$H NMR (400 MHz, DMSO-d$_6$): δ 12.32 (s, 2H), 8.73-8.66 (m, 2H), 8.11-7.98 (m, 3H), 7.52 (t, J=9.5 Hz, 5H), 7.13 (s, 2H), 6.99 (s, 1H), 5.36 (s, 2H), 2.16 (s, 3H). LC/MS: (Method B) 437.3 (M+H), RT. 4.73 min, 96.41% (Max), 93.83% (254 nm). HPLC: (Method A) RT. 2.37 min, 94.94% (Max), 95.06% (254 nm).

EXAMPLE 11

N-(1H-benzo[d]imidazol-2-yl)-3-((3-(6-((dimethylamino)methyl)pyridin-3-yl)-6-oxopyridazin-1(6H)-yl)methyl)benzamide

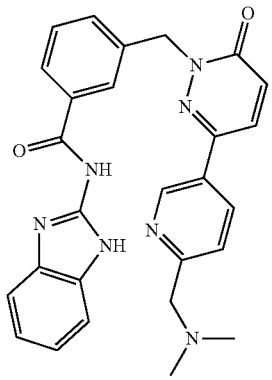 [SMILES: CN(C)Cc1ccc(-c2ccc(=O)n(Cc3cccc(C(=O)Nc4nc5ccccc5[nH]4)c3)n2)cn1]

The title compound was obtained following procedure described for intermediate 5, step 1 from N-(1H-Benzoimidazol-2-yl)-3-(3-chloro-6-oxo-6H-pyridazin-1-ylmethyl)-benzamide and Dimethyl-[5-(4,4,5,5-tetramethyl-[1,3,2]dioxaborolan-2-yl)-pyridin-2-ylmethyl]-amine as an off-white solid (103 mg, 32%). $^1$H NMR (400 MHz, DMSO-d$_6$): δ 12.29 (s, 2H), 9.01 (d, J=2.0 Hz, 1H), 8.26 (dd, J=2.3, 9.1 Hz, 1H), 8.15 (d, J=9.8 Hz, 2H), 8.07 (d, J=7.7 Hz, 1H), 7.60 (d, J=7.6 Hz, 1H), 7.54-7.47 (m, 2H), 7.44-7.41 (m, 2H), 7.16-7.11 (m, 3H), 5.42 (s, 2H), 3.56 (s, 2H), 2.19 (s, 6H). LC/MS: (Method A) 437.3 (M+H), RT. 2.34 min, 98.15% (Max), 98.58% (254 nm). HPLC: (Method A) RT. 2.38 min, 98.34% (Max), 98.69% (254 nm).

EXAMPLE 12

N-(1H-benzo[d]imidazol-2-yl)-3-((3-(4-methylpyridin-3-yl)-6-oxopyridazin-1(6H)-yl)methyl)benzamide

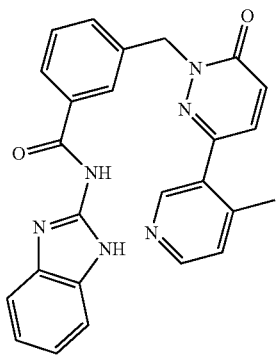 [SMILES: Cc1ccncc1-c1ccc(=O)n(Cc2cccc(C(=O)Nc3nc4ccccc4[nH]3)c2)n1]

The title compound was obtained following procedure described for intermediate 5, step 1. from N-(1H-Benzoimidazol-2-yl)-3-(3-chloro-6-oxo-6H-pyridazin-1-ylmethyl)-benzamide and 4-methyl-3-(4,4,5,5-tetramethyl-1,3,2-dioxaborolan-2-yl)pyridine (purchased from Boron Molecular) as a beige solid (12 mg, 5%). $^1$H NMR (400 MHz, DMSO-d$_6$): δ 12.35 (s, 2H), 8.59 (s, 1H), 8.49 (d, J=5.0 Hz, 1H), 8.12 (s, 1H), 8.08 (d, J=7.6 Hz, 1H), 7.80 (d, J=9.6 Hz, 1H), 7.58 (d, J=7.8 Hz, 1H), 7.51 (t, J=7.9 Hz, 1H), 7.44 (t, J=1.9 Hz, 2H), 7.35 (d, J=5.0 Hz, 1H), 7.14 (dd, J =1.9, 4.9 Hz, 3H), 5.40 (s, 2H), 2.31 (s, 3H). LC/MS: (Method A) 480.3 (M+H), RT. 2.32 min, 98.90% (Max), 99.16% (254 nm). HPLC: (Method A) RT. 2.41 min, 96.97% (Max), 97.22% (254 nm).

Example 13

N-(1H-benzo[d]imidazol-2-yl)-3-((3-(6-methylpyridazin-4-yl)-6-oxopyridazin-1(6H)-yl)methyl)benzamide

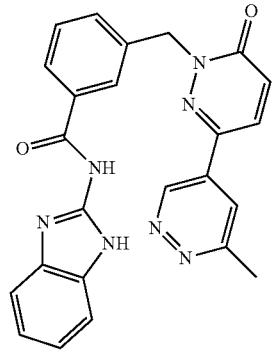 [SMILES: Cc1cc(-c2ccc(=O)n(Cc3cccc(C(=O)Nc4nc5ccccc5[nH]4)c3)n2)cnn1]

The title compound was obtained following procedure described for intermediate 5, step 1 from N-(1H-Benzoimidazol-2-yl)-3-(3-chloro-6-oxo-6H-pyridazin-1-ylmethyl)- benzamide and 3-methyl-5-(4,4,5,5-tetramethyl-1,3,2-dioxaborolan-2-yl)pyridazine (purchased from Combi-Blocks) as a white solid (35 mg, 12%). $^1$H NMR (400 MHz, DMSO-$d_6$): δ 12.30 (s, 2H), 9.58 (d, J=1.9 Hz, 1H), 8.24 (d, J=9.7 Hz, 1H), 8.14 (brs, 1H), 8.08 (d, J=7.7 Hz, 1H), 8.04 (d, J=1.9 Hz, 1H), 7.63 (d, J=7.6 Hz, 1H), 7.52 (t, J=7.6 Hz, 1H), 7.44 (m, 2H), 7.23 (d, J=9.8 Hz, 1H), 7.13-7.11 (m, 2H), 5.46 (s, 2H), 2.68 (s, 3H). LC/MS: (Method A) 438.3 (M+H), RT. 2.45 min, 96.32% (Max), 93.47% (254 nm). HPLC: (Method A) RT. 2.49 min, 94.55% (Max), 94.92% (254 nm).

EXAMPLE 14

N-(1H-benzo[d]imidazol-2-yl)-3-((3-(5-((dimethylamino)methyl)pyridin-3-yl)-6-oxopyridazin-1(6H)-yl)methyl)benzamide

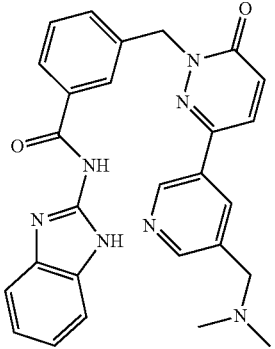 [SMILES: CN(C)Cc1cncc(-c2ccc(=O)n(Cc3cccc(C(=O)Nc4nc5ccccc5[nH]4)c3)n2)c1]

The title compound was obtained following procedure described for intermediate 5, step 1 from N-(1H-Benzoimidazol-2-yl)-3-(3-chloro-6-oxo-6H-pyridazin-1-ylmethyl)-benzamide and Dimethyl-[5-(4,4,5,5-tetramethyl-[1,3,2]dioxaborolan-2-yl)-pyridin-3-ylmethyl]-amine (purchased from Small Molecules, inc.) as a white solid (94 mg, 32%). $^1$H NMR (400 MHz, DMSO-$d_6$): δ 12.30 (s, 2H), 9.01 (d, J=1.8 Hz, 1H), 8.54 (s, 1H), 8.18-8.12 (m, 3H), 8.07 (d, J=7.7 Hz, 1H), 7.58 (d, J=7.5 Hz, 1H), 7.51 (t, J=7.6 Hz, 1H), 7.44 (m, 2H), 7.16-7.11 (m, 3H), 5.44 (s, 2H), 3.47 (s, 2H), 2.13 (s, 6H). LC/MS: (Method A) 480.2 (M+H), RT. 2.31 min, 98.46% (Max), 99.18% (254 nm). HPLC: (Method A) RT. 2.41 min, 99.04% (Max), 98.82% (254 nm).

EXAMPLE 15

N-(5,6-dimethoxy-1H-benzo[d]imidazol-2-yl)-3-((6-oxo-3-(pyridin-3-yl)pyridazin-1(6H)-yl)methyl)benzamide

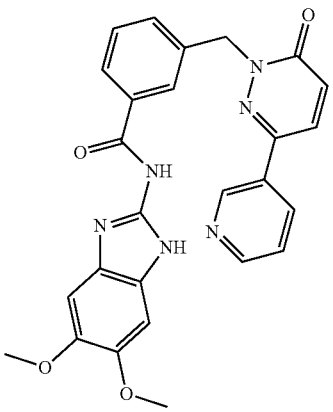 [SMILES: COc1cc2nc(NC(=O)c3cccc(Cn4nc(-c5cccnc5)ccc4=O)c3)[nH]c2cc1OC]

The title compound was obtained following procedure described for intermediate 6 from 5,6-Dimethoxy-1H-benzoimidazol-2-ylamine (purchased from Enamine) and lithium 3-(6-oxo-3-pyridin-3-yl-6H-pyridazin-1-ylmethyl)benzoate as a yellow solid (46 mg, 8%). $^1$H NMR (400 MHz, DMSO-$d_6$): δ 12.16 (s, 2H), 9.12 (d, J=1.7 Hz, 1H), 8.65 (d, J=6.3 Hz, 1H), 8.29-8.26 (m, 1H), 8.17 (d, J=9.8 Hz, 1H), 8.11 (s, 1H), 8.05 (d, J=7.8 Hz, 1H), 7.60 (d, J=6.7 Hz, 1H), 7.54-7.46 (m, 2H), 7.17 (d, J=9.7 Hz, 1H), 7.03 (s, 2H), 5.43 (s, 2H), 3.75 (s, 6H). LC/MS: (Method A) 483.3 (M+H), RT. 2.34 min, 96.83% (Max), 96.63% (254 nm). HPLC: (Method A) RT. 2.37 min, 96.48% (Max), 97.91% (254 nm).

EXAMPLE 16

N-(5-methoxy-1H-benzo[d]imidazol-2-yl)-3-((6-oxo-3-(pyridin-3-yl)pyridazin-1(6H)-yl)methyl)benzamide

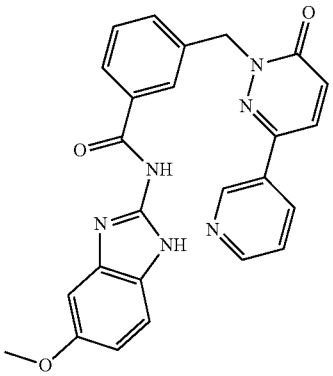 [SMILES: COc1ccc2[nH]c(NC(=O)c3cccc(Cn4nc(-c5cccnc5)ccc4=O)c3)nc2c1]

The title compound was obtained following procedure described for intermediate 6 from 5-Methoxy-1H-benzoimidazol-2-ylamine (purchased from Anichem) and lithium 3-(6-oxo-3-pyridin-3-yl-6H-pyridazin-1-ylmethyl)benzoate as a yellow solid (101 mg, 11%). $^1$H NMR (400 MHz, DMSO-$d_6$): δ 12.20 (s, 2H), 9.12 (s, 1H), 8.65 (d, J=4.5 Hz, 1H), 8.28 (d, J=8.0 Hz, 1H), 8.16 (t, J=9.8 Hz, 2H), 8.06 (d, J=7.7 Hz, 1H), 7.60 (d, J=7.5 Hz, 1H), 7.54-7.47 (m, 2H), 7.32 (d, J=8.6 Hz, 1H), 7.17 (d, J=9.8 Hz, 1H), 6.98 (d, J=1.5 Hz, 1H), 6.76 (m, 1H), 5.43 (s, 2H), 3.75 (s, 3H). LC/MS: (Method A) 453.3 (M+H), RT. 2.44 min, 97.51% (Max), 99.01% (254 nm). HPLC: (Method A) RT. 2.45 min, 99.09% (Max), 98.82% (254 nm).

EXAMPLE 17

N-(1H-Benzoimidazol-2-yl)-3-[3-(5-hydroxymethyl-pyridin-3-yl)-6-oxo-6H-pyridazin-1-ylmethyl]-benzamide

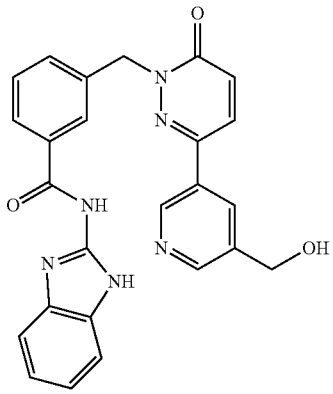 [SMILES: O=C(Nc1nc2ccccc2[nH]1)c1cccc(Cn2nc(-c3cncc(CO)c3)ccc2=O)c1]

The title compound was obtained following the procedure described for example 1 from lithium 3-[3-(5-hydroxymethyl-pyridin-3-yl)-6-oxo-6H-pyridazin-1-ylmethyl]-benzoate and 1H-benzimidazol-2-amine as off white solid (119 mg, 41%). $^1$HNMR (400 MHz, DMSO-d6): δ 12.30 (brs, 2H), 8.99 (d, J=2.1 Hz, 1H), 8.59 (d, J=1.8 Hz, 1H), 8.20 (s, 1H), 8.16 (d, J=9.8 Hz, 1H), 8.11 (s, 1H), 8.08 (d, J=7.8 Hz, 1H), 7.58 (d, J=7.6 Hz, 1H), 7.44-7.51 (m, 2H), 7.42 (t, J=3.2 Hz, 1H), 7.17-7.12 (m, 2H), 7.11 (s, 1H), 5.43 (d, J=6. Hz, 2H), 4.60 (d, J=5.2 Hz, 3H). LC/MS: (Method A) 453.0 (M+H), RT. 2.2 min, 98.7% (Max), 99.5% (254 nm). HPLC: (Method A) RT 2.2 min, 98.2% (Max), 97.6% (254 nm).

EXAMPLE 18

IRAK1 and IRAK4 Enzymatic Assays

IRAK1 Enzymatic Assay:

IRAK1 is a human purified recombinant enzyme (His-TEV-IRAK1 (194-712)) In this assay, IRAK-1 hydrolyses ATP and autophosphorylates.

Measurement of IRAK-1 inhibition is performed in streptavidin coated 384 well FlashPlate (PerkinElmer #SMP410A).

His-TEV-IRAK-1 (15 ng/well), ATP (1 µM, [$^{33}$P]ATP 0.25 µCi/well) and compounds in DMSO (range of concentrations from 20 µM to 1 nM) or controls (2% DMSO) are incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Triton-X-100 0.01%. Kinase reaction is stopped by addition of EDTA. Supernatant is discarded, plates are washed three times with 150 mM NaCl and radioactivity is then measured in a Microbeta Trilux reader.

IRAK4 Enzymatic Assay:

IRAK4 is a human purified recombinant enzyme (His-TEV-IRAK1 (194-712)

IRAK4 hydrolyses ATP, autophosphorylates and phosphorylates a Serine/Threonine generic peptidic substrate (STK: 61ST1BLC from CisBio International based in Bagnols/Cèze FR).

Measurement of IRAK-4 inhibition is performed in streptavidin coated 384 well FlashPlate (PerkinElmer #SMP410A). His-TEV-IRAK4 (20 ng/well), ATP (2 µM, [$^{33}$P]ATP 0.25 µCi/well), STK1-biotin peptide (300 nM) and compounds in DMSO (range of concentrations from 20 µM to 1 nM) or controls (2% DMSO) are incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Tween-20 0.01%, MnCl2 5 mM. Kinase reaction is stopped by addition of EDTA. Supernatant is discarded, plates are washed three times with 150 mM NaCl and radioactivity is then measured in a Microbeta Trilux reader.

EXAMPLE 19

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:

1. A compound of formula (I):

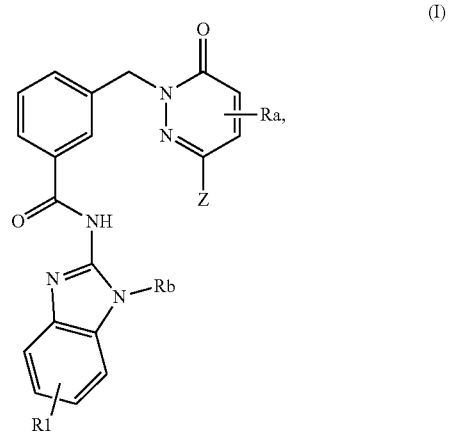

wherein Ra is H, Hal or Al, wherein Hal is F, Cl, Br, or I, and wherein Al is a branched or linear alkyl having 1 to 12 C-atoms, wherein one or more H atoms may be replaced by Hal, ORb, COORb, CN or N(Rb)$_2$ and wherein one or more CH$_2$-groups may be replaced by O, CO, NRb or S, SO, SO$_2$, 1,2-, 1,3- or 1,4- phenylen, —CH=CH— or —C≡C—, wherein Rb is H or alkyl, wherein R1 is H, Hal or Al, and wherein Z is a group:

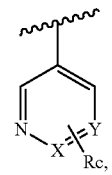

wherein in said group:

X is CH or N,

Y is CH or N, and

Rc is H, Hal or Al, and a pharmaceutically acceptable solvate, pharmaceutically acceptable salt, or stereoisomer thereof.

2. The compound of Formula (I) according to claim 1, wherein Ra is Hal, ORd, or alkyl, and wherein Rd is H, alkyl or COH or COalkyl.

3. The compound of Formula (I) according to claim 1, wherein R1 denotes H, alkyl, Hal, Oalkyl, ORd, (CH$_2$)nCONHRb or (CH2)nCOORb, wherein n is 0, 1, 2, 3, 4, 5, or 6 and Rd is H, alkyl or CORb.

4. The compound of Formula (I) according to claim 1, wherein Z is pyridinyl or pyrimidinyl.

5. The compound of Formula (I) according to claim 1, selected from the group consisting of compounds 1, 2, 3, 4, 5, 6, 7, 8, 9, 10, 11, 12, 13, 14, 15, 16, 17 and a pharmaceutically acceptable solvate, pharmaceutically acceptable salt, or stereoisomer thereof, wherein compounds 1, 2, 3, 4, 5, 6, 7, 8, 9, 10, 11, 12, 13, 14, 15, 16, 17 are:

1

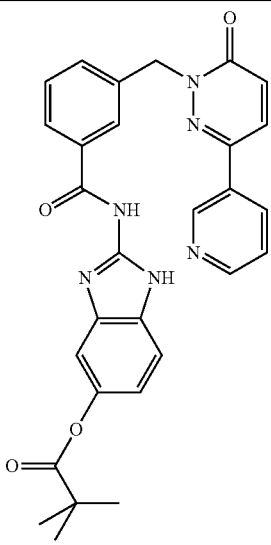

2

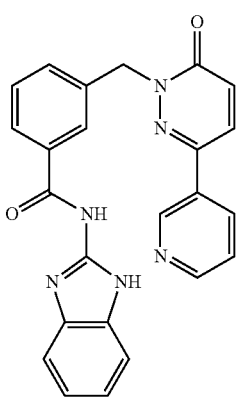 [SMILES: O=C(Nc1nc2ccccc2[nH]1)c1cccc(Cn2nc(-c3cccnc3)ccc2=O)c1]

3

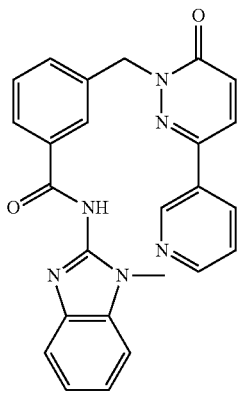 [SMILES: Cn1c(NC(=O)c2cccc(Cn3nc(-c4cccnc4)ccc3=O)c2)nc2ccccc21]

4

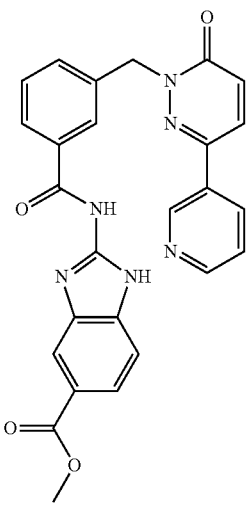 [SMILES: COC(=O)c1ccc2[nH]c(NC(=O)c3cccc(Cn4nc(-c5cccnc5)ccc4=O)c3)nc2c1]

5

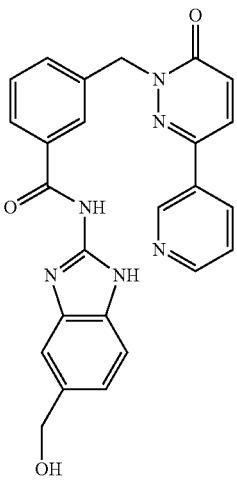 [SMILES: O=C(Nc1nc2cc(CO)ccc2[nH]1)c1cccc(Cn2nc(-c3cccnc3)ccc2=O)c1]

-continued
| 6 | 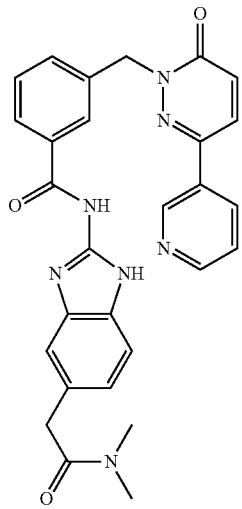 [SMILES: CN(C)C(=O)Cc1ccc2[nH]c(NC(=O)c3cccc(Cn4nc(-c5cccnc5)ccc4=O)c3)nc2c1] |
| 7 | 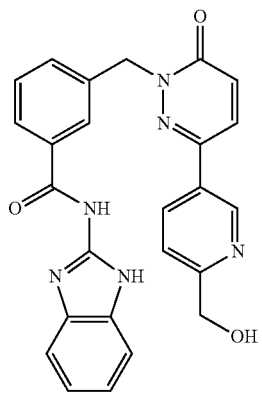 [SMILES: O=C(Nc1nc2ccccc2[nH]1)c1cccc(Cn2nc(-c3ccc(CO)nc3)ccc2=O)c1] |
| 8 | 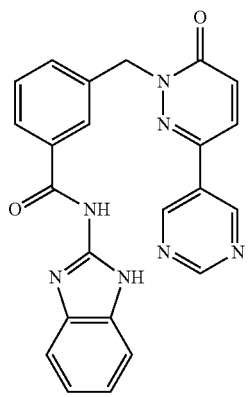 [SMILES: O=C(Nc1nc2ccccc2[nH]1)c1cccc(Cn2nc(-c3cncnc3)ccc2=O)c1] |
-continued
| 9 | 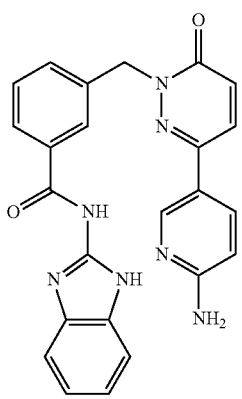 [SMILES: Nc1ccc(-c2ccc(=O)n(Cc3cccc(C(=O)Nc4nc5ccccc5[nH]4)c3)n2)cn1] |
| 10 | 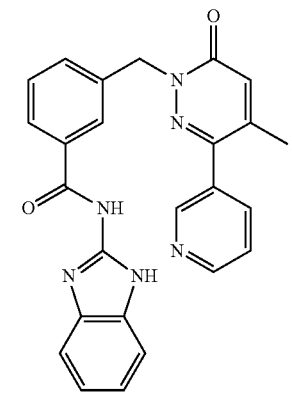 [SMILES: Cc1cc(=O)n(Cc2cccc(C(=O)Nc3nc4ccccc4[nH]3)c2)nc1-c1cccnc1] |
| 11 | 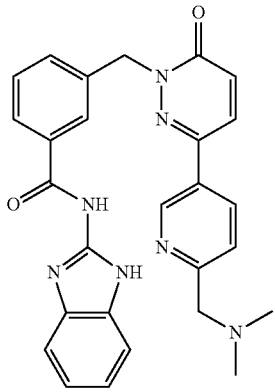 [SMILES: CN(C)Cc1ccc(-c2ccc(=O)n(Cc3cccc(C(=O)Nc4nc5ccccc5[nH]4)c3)n2)cn1] |
| 12 | 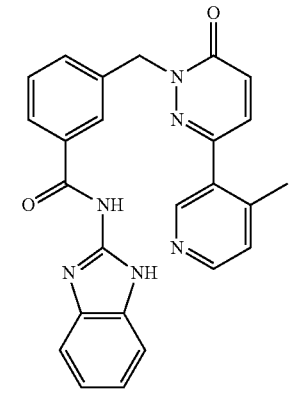 [SMILES: Cc1ccncc1-c1ccc(=O)n(Cc2cccc(C(=O)Nc3nc4ccccc4[nH]3)c2)n1] |

13

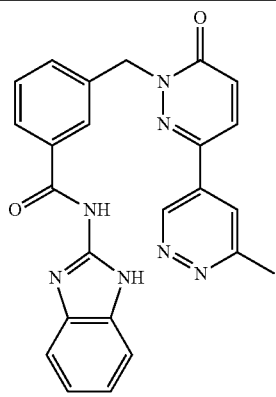

14

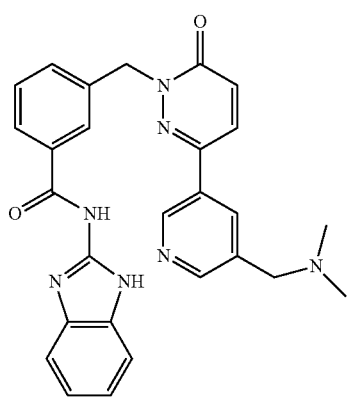 [SMILES: CN(C)Cc1cncc(-c2ccc(=O)n(Cc3cccc(C(=O)Nc4nc5ccccc5[nH]4)c3)n2)c1]

15

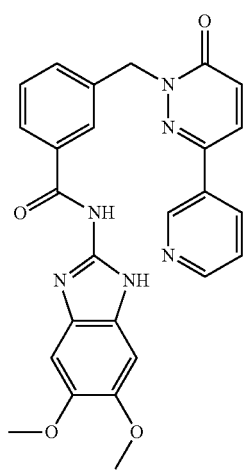 [SMILES: COc1cc2nc(NC(=O)c3cccc(Cn4nc(-c5cccnc5)ccc4=O)c3)[nH]c2cc1OC]

16

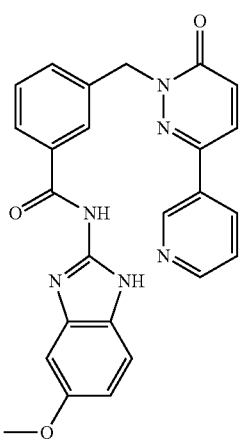 [SMILES: COc1ccc2[nH]c(NC(=O)c3cccc(Cn4nc(-c5cccnc5)ccc4=O)c3)nc2c1]

17

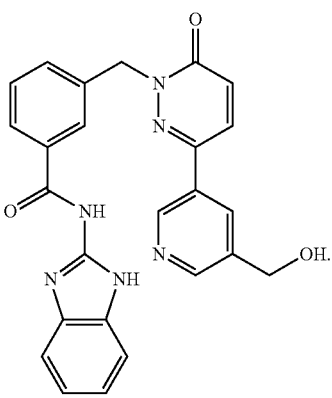 [SMILES: O=C(Nc1nc2ccccc2[nH]1)c1cccc(Cn2nc(-c3cncc(CO)c3)ccc2=O)c1]

6. A pharmaceutical composition, comprising:
the compound of Formula (I) according to claim 1 and a pharmaceutically acceptable solvate, salt, hydrate or stereoisomer thereof, including mixtures thereof in all ratios.

7. A method for the treatment of rheumatoid arthritis, lupus nephritis, and systemic lupus erythematosus comprising administering the composition according to claim 6 to a subject in need thereof.

* * * * *